US008523769B2

(12) United States Patent
Fehling et al.

(10) Patent No.: US 8,523,769 B2
(45) Date of Patent: Sep. 3, 2013

(54) SPREADER FOR AORTIC VALVE RECONSTRUCTION

(75) Inventors: Gerald Fehling, Aschaffenburg (DE); Ulrike Lindner, Karlstein (DE)

(73) Assignee: Fehling Instruments GmbH & Co. KG, Karlstein (DE)

( * ) Notice: Subject to any disclaimer, the term of this patent is extended or adjusted under 35 U.S.C. 154(b) by 271 days.

(21) Appl. No.: 13/047,233

(22) Filed: Mar. 14, 2011

(65) Prior Publication Data

US 2011/0237903 A1    Sep. 29, 2011

(30) Foreign Application Priority Data

Mar. 24, 2010    (DE) .......................... 10 2010 012 677

(51) Int. Cl.
*A61B 1/32*    (2006.01)

(52) U.S. Cl.
USPC ............ 600/224; 600/235; 600/217; 600/210

(58) Field of Classification Search
USPC ................. 600/201, 204, 208, 210, 213–215, 600/217–219, 222, 224, 231, 233, 235
See application file for complete search history.

(56) References Cited

U.S. PATENT DOCUMENTS

| 5,580,344 | A  | * | 12/1996 | Hasson ........................ 600/219 |
| 6,342,036 | B1 | * | 1/2002  | Cooper et al. ................ 600/224 |
| 2005/0096508 | A1 |   | 5/2005 | Valentini et al. |
| 2005/0215866 | A1 | * | 9/2005 | Kim ............................... 600/233 |
| 2010/0217089 | A1 | * | 8/2010 | Farley et al. .................. 600/213 |
| 2011/0105850 | A1 | * | 5/2011 | Voegele et al. ............... 600/207 |

* cited by examiner

*Primary Examiner* — Ellen C Hammond
(74) *Attorney, Agent, or Firm* — Akerman Senterfitt; Peter A. Chiabotti

(57) ABSTRACT

A spreader for aortic valve reconstruction having a dimensionally stable ring and three retractor arms comprising, respectively, a stem and a blade, with the blade being distally disposed on the stem, and wherein the retractor arms are disposed, offset relative to each other by respectively 120° in the direction of circumference of the ring, on said ring, and wherein the stems of the retractor arms are substantially aligned as perpendicular relative to the plane of the ring, and wherein the retractor arms are supported on the ring in such a way by the proximal end of their stems that they can be radially moved relative to each other toward the inside and radially expanded by the spring force of the ring.

8 Claims, 3 Drawing Sheets

SPREADER FOR AORTIC VALVE RECONSTRUCTION

CROSS REFERENCE TO RELATED APPLICATIONS

This application claims the benefit of German Patent Application No. DE 10 2010 012 677.2 filed Mar. 24, 2010, which is hereby incorporated by reference in its entirety.

DESCRIPTION

The invention relates to a spreader for aortic valve reconstruction.

Nowadays, surgery of the aortic valve is among the routine procedures in cardiac surgery. Frequently it is necessary to replace a failing aortic valve with a mechanical or biological heart valve. But, insofar as possible, the goal is to preserve the patient's own aortic valve and to functionally reconstruct it. This is especially an option for the treatment of deformations of the leaflets, provided they do not yet show signs of severe degeneration, and their elasticity is still intact. With this type of aortic valve reconstruction formally and functionally sufficient aortic leaflets are surgically modeled from the patient's own valve tissue or pericardial tissue.

The leaflets are attached to the annulus fibrosus by a half-moon-shaped connection zone. To achieve optimum valve closure with a reconstruction of the leaflets, it is necessary for the annulus fibrosus to be held as much as possible in its natural location and position during modeling.

The underlying object of the present invention is therefore to provide a surgical instrument that simplifies the aortic valve reconstruction and is able to improve the surgical outcome.

SUMMARY OF THE INVENTION

According to the invention this object is achieved by providing a spreader for aortic valve reconstruction having the structures and features described herein.

According to the invention the surgeon is provided with a spreader that is inserted through the surgically opened ascending aorta and into the aortic valve. The spreader comprises a dimensionally stable ring that has three retractor arms disposed thereon. The retractor arms comprise each a stem that is aligned almost as perpendicular relative to the plane of the ring, and at the free distal end of which there is configured an outwardly curved blade. The three retractor arms are supported on the ring with the capability for radial displacement; in particular, they are pre-loaded by spring power allowing them to be radially moved inside the ring in an outward direction. The three retractor arms can thereby be radially pressed toward the inside against the spring load so that that they come to lie adjacent to each other in proximity of the center axis of the spreader. The retractor arms that are pushed together in this way into a narrow outside diameter can thus be inserted by their respective blades in the annulus fibrosus. Upon being released, due to the spring force, the retractor arms are radially moved in the outward direction again and spread apart so that they place themselves by their blades against the annulus fibrosus, thereby holding the ring spread open. Upon being inserted, the spreader is aligned in its rotational angle position in such a way that the three retractor arms engage by their respective blades on the annulus fibrosus, specifically in those places where the three leaflets attach. This ensures that the annulus fibrosus will be held and supported in its natural position in the areas of the leaflets. During the surgery the spreader remains in its position and holds, in reliance on its spring effect, the annulus fibrosus automatically spread open without any need for additional assistance.

The retractor arms are preferably attached to sliders that are supported on the ring with the ability for radial displacement. In this context, the spring force is provided, in terms of construction, in an easy manner by configuring a spring that supports the slider on the ring.

Preferably the retractor arms are replaceably attached on the slider, thereby allowing for easy cleaning and sterilization. The use of retractor arms in different forms and sizes in connection with the same ring and the same sliders is also possible. This configuration is also suitable if the retractor arms are disposable items for one-time use.

BRIEF DESCRIPTION OF DRAWINGS

Subsequently, the invention will be illustrated in further detail using an embodied example as shown in the drawing. Shown in.

DETAILED DESCRIPTION

Figure 1:
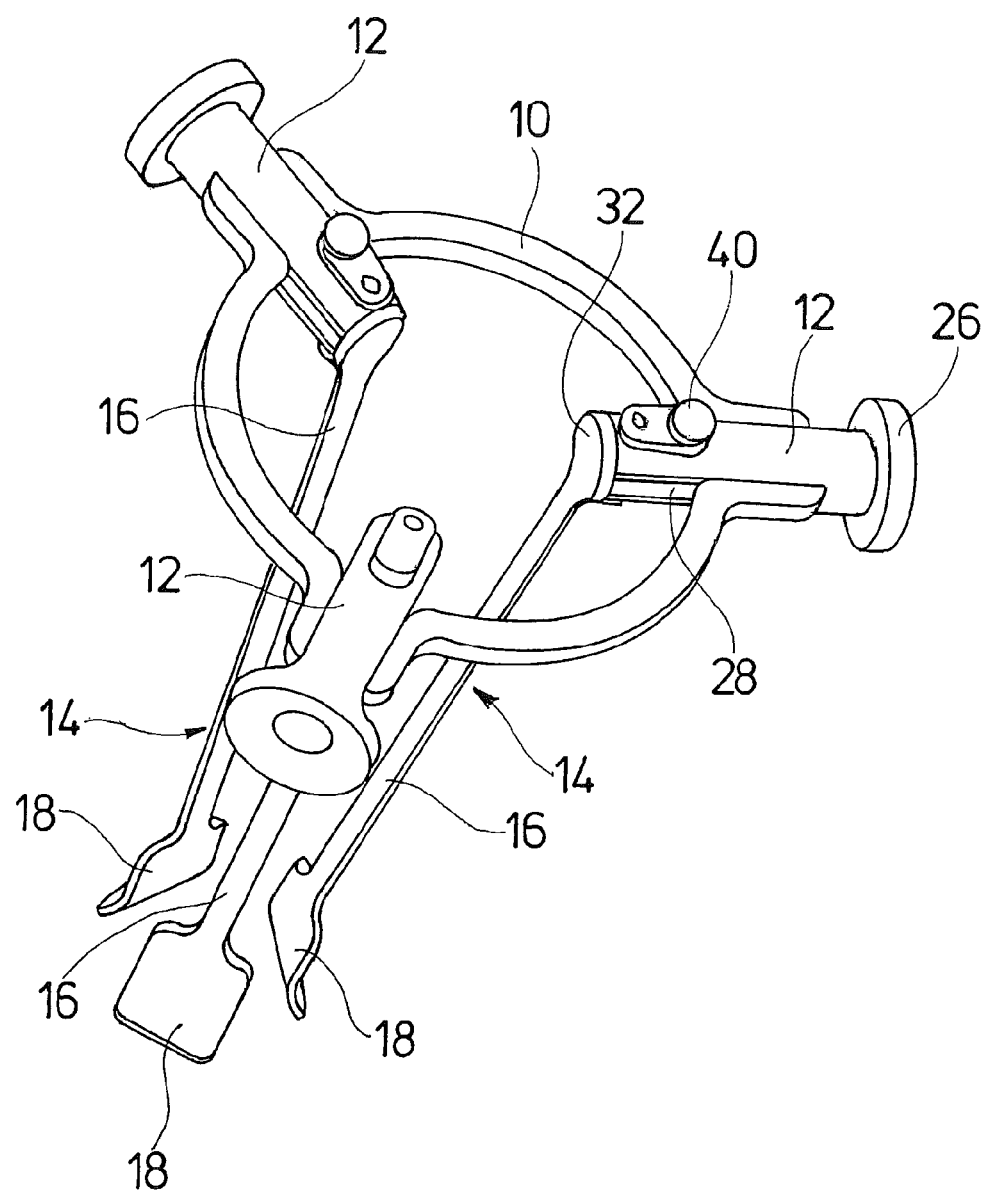
FIG. 1 a total view of the spreader.

The spreader as shown in FIG. 1 for aortic valve reconstruction comprises a dimensionally stable ring 10 with an open free inside diameter of between 40 mm and 80 mm; for example, approximately 65 mm. The sliders 12 are supported on the ring 10, respectively offset relative to each other by an angle of 120°. The sliders 12 are held in the plane of ring 10 as radially displaceable in relation to the center point. Respectively one retractor arm 14 is attached at each of the inside ends of the sliders 12. The retractor arms 14 are made, respectively, of a dimensionally stable material, specifically a metal and preferably stainless steel. The retractor arms 14 comprise a long-extended, thin stem 16 of a length of approximately 50 mm to 100 mm. The stems 16 are replaceably attached by their proximal ends to the radial inside end of the respective slider 12. At the free distal end of the stems 16 a respective blade 18 is disposed, manufactured in one piece with the stems. The blades 18 are approximately 8 mm to 12 mm wide, preferably approximately 10 mm. The blades 18 have a height of approximately 8 mm to 12 mm. The blades 18 are disposed in such a manner that their plane essentially extends in a tangential direction relative to the ring 10. At their distal free edge the blades 18 are slightly bend toward the outside. The stems 16 extend approximately perpendicular relative to the plane of the ring 10. It is preferred for the stems 16 to be pointed away relative to the radial displacement axis of the sliders 12 at an angle of approximately 90° to 110° in order to allow for their distal ends that are configured with the blade 18 to be located in closer proximity to the center axis of the ring 10 than their proximal ends that are attached to the sliders 12.

The sliders 12 can be displaced from their insertion position to their spread-out position via a radial lift path. In the insertion position the sliders 12 are pushed to the maximum inside position against the longitudinal center axis of the ring 10. In this insertion position the blades 18 have a radial distance relative to the longitudinal center axis of the ring of between 7 mm to 9 mm respectively, specifically approximately 8 mm. In the spread-out position the sliders 12 are extended radially to their maximum outward position. In this spread-out position the blades 18 are at a radial distance relative to each other of approximately 9 mm to 19 mm, specifically of approximately 13 mm, relative to the longitudinal center axis of the ring 10.

Figure 2:
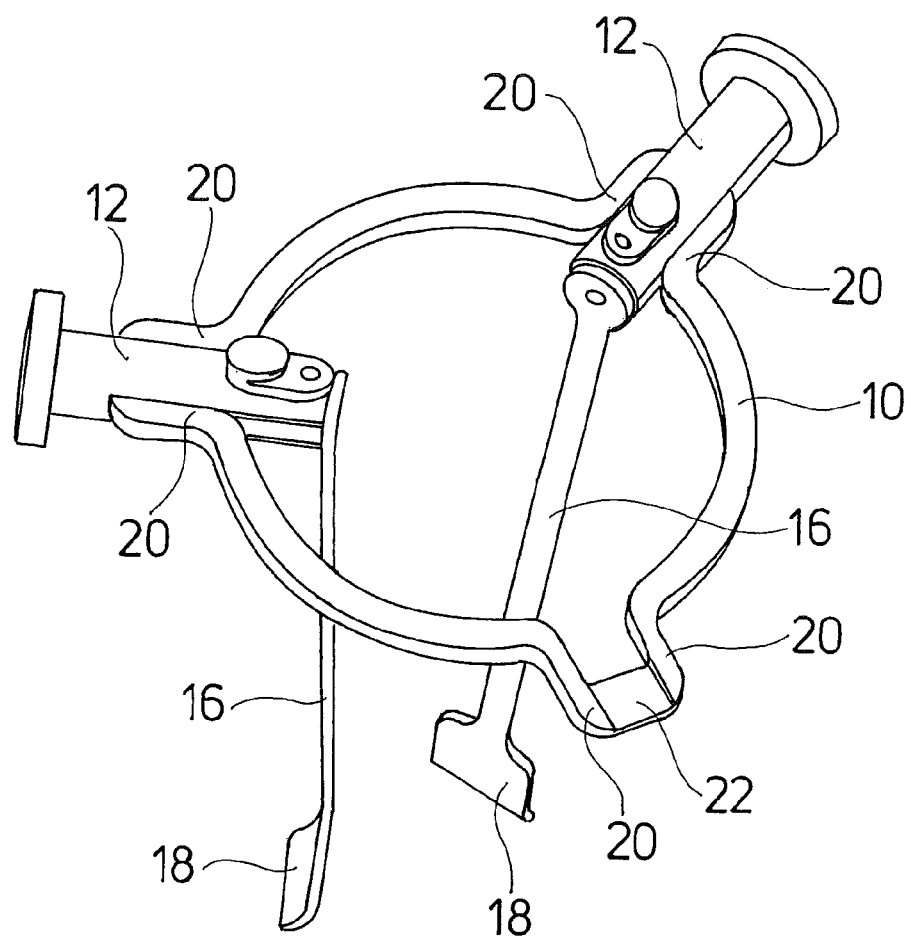
FIG. 2 a corresponding view of the spreader with, for purposes of clarification, a removed slider with retractor arm.

FIG. 1 shows the spreader with all three sliders 12, and wherein all three sliders are in the same radial position. FIG. 2, on the other hand, depicts only two sliders, and wherein these two sliders are in different radial positions. The third slider 12 has been omitted from FIG. 2 for a visual demonstration of how the slider 12 is guided in the ring 10.

Figure 3:
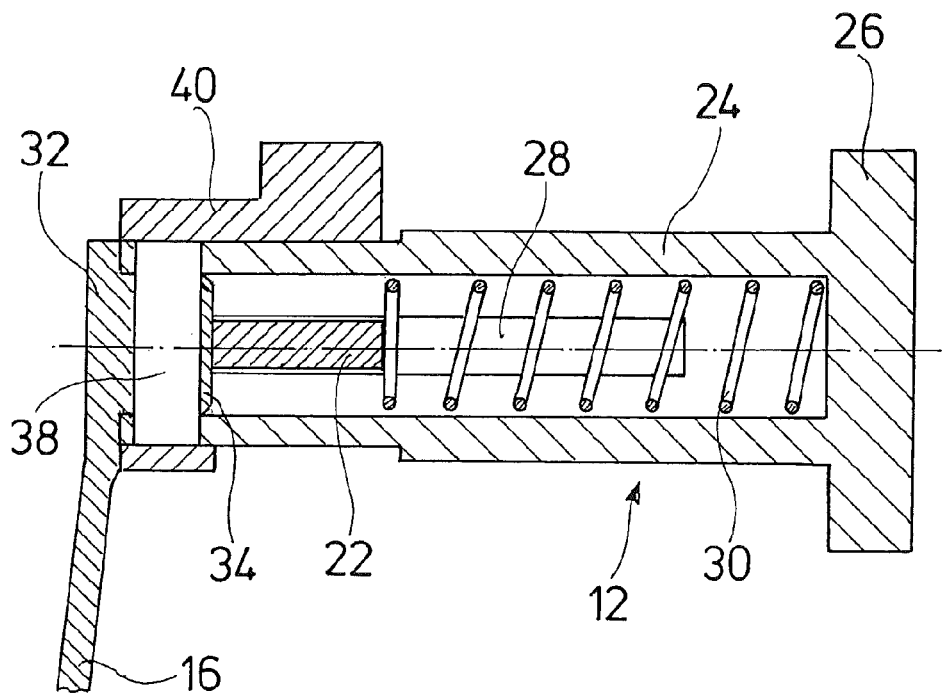
FIG. 3 a vertical axial section of a slider.
Figure 4:
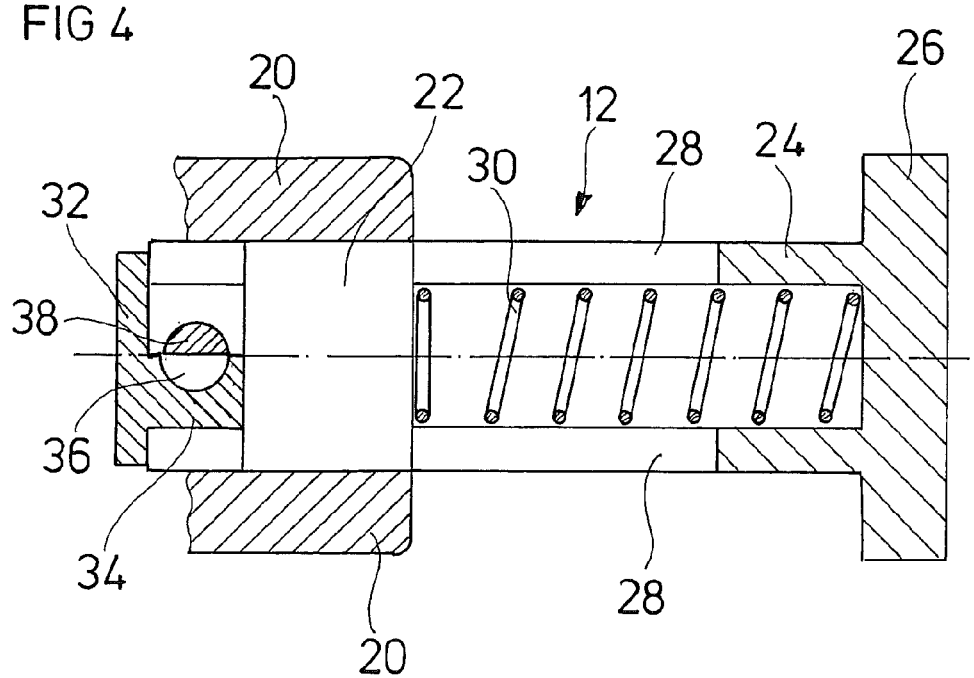
FIG. 4 a horizontal axial section of the slider.

The FIGS. 3 and 4 show the configuration of the sliders 12 in detail.

As can be seen in FIG. 2, the ring 10 comprises two cheeks 20 that are radially and outwardly directed at the angle positions of the sliders 12, which are offset by 120° relative to each other; the cheeks extend parallel relative to each other and are connected by a flattened, radially widened bar 22 at their radially outer end. The slider 12 has a hollow, circular-cylindrical sleeve 24 with an outside diameter that corresponds to the inside clearance of the cheeks 20. The sleeve 24 is closed at its radially outer end and configured with a radially widened finger support 26. Starting at the radially inner end, the sleeve 24 is configured with an axial slot 28. The slot 28 extends axially into the sleeve 24 until almost to the sleeve's radial outer end. The width of slot 28 corresponds to the thickness of bar 22; the sleeve 24 can thus be moved radially from the outside onto the bar 22 by the slot 28, where it is radially and un-tiltably guided. Inserted coaxially in the sleeve 24 is a screw pressure spring 30. The screw pressure spring 30 is supported by its radial outer end inside on the closed end of the sleeve 24, while the screw pressure spring 30 supports itself by its inner end on the bar 22. The sleeve 24 can therefore be radially pressed to the inside against the spring force of the screw pressure spring 30 relative to the bar 22 and therefore relative to the ring 10. If the slider 12 is released, the screw pressure spring 30 presses the sleeve 24 relative to the bar 22, and therefore relative to ring 10, radially to the outside.

At the proximal end of the stem 16 of the retractor arms 14, these arms are widened, respectively, to a circular disc 32 having an outside diameter that corresponds approximately to the outside diameter of the sleeve 24. With this disc 32 the stems 16 are supported on the interior front surface of the sleeve 24. A peg 34 is formed in one piece with the disc 32, which engages in the interior hollow space of the sleeve 24. As is best seen in FIG. 4, the peg 34 is in the shape of a half-cylinder the outside diameter of which corresponds to the inside diameter of the sleeve 24, but wherein only one axial half of the cylinder is present. A diametrical groove 36 is configured in the axial dividing plane of the peg 34 having a half-circular cross-section. In the axial position of the groove 36, the sleeve has located in its jacket a diametrically continuous bore hole into which locking bolt 38 is inserted. The locking bolt 38 has the shape of a half cylinder with a radius that corresponds to the radius of the groove 36. The axis of the locking bolt 38 is congruent with the axis of the groove 36. The locking bolt 38 is axially supported inside sleeve 24, specifically in that at its end that extends outside of the sleeve 24 it is widened, while at the opposite end of the locking bolt 38 there is disposed, with torsional strength, a locking lever 40 that can be swung around the axis of locking bolt 38.

To assemble the spreader the screw pressure spring 30 is first inserted in the sleeve 24. Then sleeve 24 is pressed onto bar 22 of ring 10. Subsequently, locking bolt 38 is inserted diametrically in the sleeve 24. The locking bolt 38 is swung in the release position as shown in FIG. 4 by way of locking lever 40. In this release position it is now possible for the retractor arm 14 to be inserted by its peg 34 in the sleeve 24, and wherein the axially halved peg 34 is able to push itself by the axially halved locking bolt 38. Then the locking lever 40 is swung by 180° in the locking position as shown in the FIGS. 1, 2 and 3, and in which position the axially halved locking bolt 38 engages in the groove 36 of the peg 34 causing the retractor arm 14 to be fastened by its peg 34 on sleeve 24 of slider 12. Now the spreader is functionally ready.

The retractor arms 14 can be replaced at any time. To this end, only the locking lever 40 is swung by 180° from its locked position, as shown in FIGS. 1 to 3, into the release position where the locking bolt 38 now assumes the position as shown in FIG. 4. The retractor arm 14 can now be pulled out of the sleeve 24 by its peg 34 and another retractor arm 14 can be inserted and locked by swinging the locking lever 40 in the sleeve 24 of slider 12.

During aortic valve reconstruction surgery, after the ascending aorta has been opened, the spreader is inserted in the aortic valve. To this end, the three sliders 12 are pushed radially to the inside, against the force of the screw pressure springs 30, into the insertion position resulting in the blades 18 of the retractor arms 14 to be arranged as closely as possible adjacent to each other and in close proximity to the longitudinal central axis of the spreader. Now it is possible to insert the retractor arms 14 in the aortic valve until the blades 18 are located in the area of the annulus fibrosus. During this, the spreader is rotated in such a way that the three blades 18 are located, respectively, in the angle positions of the leaflets. The sliders 12 are then released allowing them to move radially, under the force of the screw pressure spring 30, toward the outside into the spread-out position. This causes the retractor arms 14 to be moved radially as well and with their blades 18 toward the outside, whereby they expand the annulus fibrosus with the force of the screw pressure springs 30. After completion of the valve reconstruction surgery the spreader is once again removed; to achieve this the sliders 12 are once again compressed manually against the force of the screw pressure spring 30 and brought in to their starting position.

LIST OF THE REFERENCE SIGNS

10 Ring
12 Slider
14 Retractor arm
16 Stem
18 Blade
20 Cheeks
22 Bar
24 Sleeve
26 Finger support
28 Slot
30 Screw pressure spring
32 Disc
34 Peg
36 Groove
38 Locking bolt
40 Locking lever

The invention claimed is:

1. A spreader for aortic valve reconstruction, comprising:
a dimensionally stable ring;
three retractor arms disposed on the ring, offset relative to each other respectively by approximately 120° in a direction of a circumference of the ring, each retractor arm, respectively, having a stem and a blade disposed distally on the stem, wherein the stems of the retractor arms are aligned approximately perpendicular relative to a plane of the ring, and wherein the retractor arms are supported on the ring by a proximal end of their stems in such a way that the retractor arms can be moved towards a center of the ring relative to each other against a spring force in the ring and displaced radially outward by the spring force without manual intervention.

2. The spreader according to claim 1, wherein the retractor arms are each fastened to a slider that is supported, radially displaceable against the spring force, on the ring.

3. The spreader according to claim 2, wherein the retractor arms are replaceably attached on the respective slider.

4. The spreader according to claim 2, wherein the slider is configured as a hollow sleeve that is supported on the ring and displaceable via an axial slot, and wherein a spring that is inserted in the sleeve presses the sleeve radially outward.

5. The spreader according to claim 4, wherein the spring is a screw pressure spring.

6. The spreader according to claim 3, wherein the retractor arm can be inserted in a radially inner end of the sleeve via a peg, and wherein the peg can be locked by a locking bolt that passes diametrically through the sleeve.

7. The spreader according to claim 1, wherein the stems of the retractor arms enclose an angle of between approximately 90° to 110° with a radial direction of movement that is located in the plane of the ring.

8. A spreader for aortic valve reconstruction, comprising:
a dimensionally stable ring;
three retractor arms disposed on the ring, offset relative to each other respectively by approximately 120° in a direction of a circumference of the ring, each retractor arm, respectively, having a stem and a blade disposed distally on the stem, wherein the stems of the retractor arms are aligned approximately perpendicular relative to a plane of the ring, wherein the retractor arms are supported on the ring by a proximal end of their stems in such a way that the retractor arms can be moved towards a center of the ring relative to each other against a spring force in the ring and displaced radially outward expanded by the spring force, wherein the retractor arms are each fastened to a slider that is supported, radially displaceable against the spring force, on the ring, wherein the slider is configured as a hollow sleeve that is supported on the ring and displaceable via an axial slot, and wherein a spring that is inserted in the sleeve presses the sleeve radially outward, and wherein the retractor arm can be inserted in a radially inner end of the sleeve via a peg, and wherein the peg can be locked by a locking bolt that passes diametrically through the sleeve.

* * * * *